US011883395B2

(12) United States Patent
Anathy et al.

(10) Patent No.: US 11,883,395 B2
(45) Date of Patent: Jan. 30, 2024

(54) METHOD OF TREATING SEVERE ACUTE RESPIRATORY SYNDROME (SARS) VIRUS INFECTION BY ADMINISTERING A PROTEIN DISULFIDE ISOMERASE (PDI) INHIBITOR

(71) Applicant: The University of Vermont and State Agricultural College, Burlington, VT (US)

(72) Inventors: Vikas Anathy, Essex Junction, VT (US); Nicolas Chamberlain, Burlington, VT (US); Amit Kumar, Burlington, VT (US)

(73) Assignee: The University of Vermont and State Agricultural College, Burlington, VT (US)

( * ) Notice: Subject to any disclaimer, the term of this patent is extended or adjusted under 35 U.S.C. 154(b) by 75 days.

(21) Appl. No.: 17/320,069

(22) Filed: May 13, 2021

(65) Prior Publication Data

US 2021/0353620 A1 Nov. 18, 2021

Related U.S. Application Data

(60) Provisional application No. 63/024,945, filed on May 14, 2020.

(51) Int. Cl.

| | |
|---|---|
| *A61K 31/496* | (2006.01) |
| *C07K 16/40* | (2006.01) |
| *A61K 31/381* | (2006.01) |
| *A61K 31/427* | (2006.01) |
| *A61K 31/675* | (2006.01) |
| *A61K 31/7068* | (2006.01) |
| *A61K 39/395* | (2006.01) |
| *A61K 31/4965* | (2006.01) |
| *A61K 31/7048* | (2006.01) |
| *C12N 15/113* | (2010.01) |
| *A61K 35/16* | (2015.01) |
| *A61K 39/42* | (2006.01) |
| *A61P 31/14* | (2006.01) |
| *G01N 33/50* | (2006.01) |

(52) U.S. Cl.
CPC .......... *A61K 31/496* (2013.01); *A61K 31/381* (2013.01); *A61K 31/427* (2013.01); *A61K 31/4965* (2013.01); *A61K 31/675* (2013.01); *A61K 31/7048* (2013.01); *A61K 31/7068* (2013.01); *A61K 35/16* (2013.01); *A61K 39/3955* (2013.01); *A61K 39/42* (2013.01); *A61P 31/14* (2018.01); *C07K 16/40* (2013.01); *C12N 15/1137* (2013.01); *G01N 33/5008* (2013.01); *C12N 2310/14* (2013.01)

(58) Field of Classification Search
CPC .. A61K 31/496; A61K 31/381; A61K 31/427; A61K 31/4965; A61K 31/675; A61K 31/7048; A61K 31/7068; A61K 35/16; A61K 39/3955; A61K 39/42; A61P 31/14; C07K 16/40; C12N 15/1137; C12N 2310/14; G01N 33/5008

See application file for complete search history.

(56) References Cited

PUBLICATIONS

Fenouillet E, et al. (2007) Antioxidants & Redox Signaling. 9(8):1009-1034. (DOI: 10.1089/ars.2007.1639).*

Stolf BS, et al. (2011) TheScientificWorldJournal. 11:1749-1761. (doi:10.1100/2011/289182).*

Vatolin S. et al. (Jun. 1, 2016) Cancer Res. 76(11):3340-3350. (doi: 10.1158/0008-5472.CAN-15-3099).*

Gordon CJ, et al. (Apr. 13, 2020) J. Biol. Chem. 295(20):6785-6797. (DOI 10.1074/jbc.RA120.013679).*

Chamberlain et al., Lung epithelial protein disulfide isomerase A3 (PDIA3) plays an important role in influenza infection, inflammation, and airway mechanics. Redox Biol. Apr. 2019;22:101129. doi: 10.1016/j.redox.2019.101129. Epub Jan. 29, 2019.

Chamberlain et al., Pathological consequences of the unfolded protein response and downstream protein disulphide isomerases in pulmonary viral infection and disease. J Biochem. Feb. 1, 2020;167(2):173-184. doi: 10.1093/jb/mvz101.

Giamogante et al., Punicalagin, an active pomegranate component, is a new inhibitor of PDIA3 reductase activity. Biochimie. Apr. 2018;147:122-129. doi: 10.1016/j.biochi.2018.01.008. Epub Feb. 6, 2018.

Hamming et al., Tissue distribution of ACE2 protein, the functional receptor for SARS coronavirus. A first step in understanding SARS pathogenesis. J Pathol. Jun. 2004;203(2):631-7. doi: 10.1002/path.1570.

Hoffmann et al., SARS-COV-2 Cell Entry Depends on ACE2 and TMPRSS2 and Is Blocked by a Clinically Proven Protease Inhibitor. Cell. Apr. 16, 2020;181(2):271-280.e8. doi: 10.1016/j.cell.2020.02.052. Epub Mar. 5, 2020.

Kaplan et al., Small molecule-induced oxidation of protein disulfide isomerase is neuroprotective. Proc Natl Acad Sci U S A. Apr. 28, 2015;112(17):E2245-52. doi: 10.1073/pnas.1500439112. Epub Apr. 6, 2015.

(Continued)

*Primary Examiner* — Robert S Landsman
(74) *Attorney, Agent, or Firm* — Wolf, Greenfield & Sacks, P.C.

(57) ABSTRACT

Compositions and methods involving protein disulfide isomerase (PDI) inhibitors, such as protein disulfide isomerase A3 (PDIA3) inhibitory compounds, for human coronavirus, such as severe acute respiratory syndrome (SARS) virus (e.g., SARS-CoV-2), therapies are disclosed herein.

19 Claims, 1 Drawing Sheet

(56) References Cited

PUBLICATIONS

Kim et al., Protein disulfide isomerases as potential therapeutic targets for influenza A and B viruses. Virus Res. Mar. 2, 2018;247:26-33. doi: 10.1016/j.virusres.2018.01.010. Epub Jan. 31, 2018. Author Manuscript. 19 pages.

Sanders et al., Pharmacologic Treatments for Coronavirus Disease 2019 (COVID-19): A Review. JAMA. May 12, 2020;323(18):1824-1836. doi: 10.1001/jama.2020.6019. PMID: 32282022.

Yang et al., Mice transgenic for human angiotensin-converting enzyme 2 provide a model for SARS coronavirus infection. Comp Med. Oct. 2007;57(5):450-9.

* cited by examiner

METHOD OF TREATING SEVERE ACUTE RESPIRATORY SYNDROME (SARS) VIRUS INFECTION BY ADMINISTERING A PROTEIN DISULFIDE ISOMERASE (PDI) INHIBITOR

RELATED APPLICATION

This application claims the benefit under 35 U.S.C. § 119(e) of U.S. provisional application No. 63/024,945, filed May 14, 2020, which is incorporated herein by reference in its entirety.

FEDERALLY SPONSORED RESEARCH

This invention was made with government support under R01 Grant HL141364, awarded by the National Institutes of Health/National Heart, Lung, and Blood Institute (NIH/MHLBI). Accordingly, the government has certain rights in the invention.

BACKGROUND OF THE INVENTION

Coronavirus disease 2019 (COVID-19), an infectious disease caused by the severe acute respiratory syndrome coronavirus 2 (SARS-CoV-2) strain, has spread to six continents, with more than two million cases, with approximately 250,000 reported deaths as early May 2020. Symptoms of COVID-19 can range from mild to severe. Severe symptoms include acute lung injury (ALI) and subsequent acute respiratory distress syndrome (ARDS), which accounts for the majority of the respiratory failure and mortality related to SARS-CoV-2 infection.

SUMMARY OF THE INVENTION

The disclosure, in some aspects, relates to a method of treating a human coronavirus infection, such as a severe acute respiratory syndrome (SARS) virus infection, the method comprising administering to a subject in need thereof, a composition comprising a protein disulfide isomerase (PDI) inhibitor and a pharmaceutically acceptable excipient. In some embodiments, the PDI inhibitor is a small molecule inhibitor, an anti-PDI antibody, or an inhibitory nucleic acid. In one embodiment, the inhibitory nucleic acid is a small interfering RNA (siRNA).

In some embodiments, the PDI inhibitor is a protein disulfide isomerase A3 (PDIA3) inhibitor. In some embodiments, the PDIA3 inhibitor is lead optimized compound 14 (LOC14) or variant thereof. In some embodiments, the PDIA3 inhibitor is selected from the group consisting of: PACMA31 and CCF642.

In some embodiments, the method further comprises a second anti-viral component. In another embodiment, the second anti-viral component is selected from the group consisting of: remdesivir, $\beta$-D-N$^4$-hydroxycytidine, convalescent plasma, Covid-19 monoclonal antibodies, and favipiravir.

In some embodiments, the severe acute respiratory syndrome (SARS) virus is the severe acute respiratory syndrome coronavirus 2 (SARS-CoV-2) virus.

In some embodiments, the PDIA3 inhibitor is a reversible inhibitor. In some embodiments, the PDIA3 inhibitor is a selective PDIA3 inhibitor. In some embodiments, the selective PDIA3 inhibitor binds with a higher affinity to PDIA3 than PDIA1.

Another aspect of the disclosure provides a method for identifying a SARS therapeutic agent, comprising, determining a level of PDIA3 inhibition in a cell or in vitro assay in response to exposure of the PDIA3 to a putative agent, and wherein the level of PDIA3 relative to a baseline level is lower than the baseline, the putative agent is a SARS therapeutic agent.

An additional aspect of the disclosure provides an anti-SARS (e.g., anti-SARS-CoV-2) composition comprising at least one protein disulfide isomerase A3 (PDIA3) inhibitor, an anti-viral component and a pharmaceutically acceptable excipient. In some embodiments, the anti-SARS composition reduces the severity or prevents SARS infections caused by a SARS strain, wherein the influenza infection is caused by a drift-variant of the strain present in an immunogenic composition of influenza vaccine.

In some embodiments, the PDIA3 inhibitor is lead optimized compound 14 (LOC14) or a variant thereof. In another embodiment, the PDIA3 inhibitor is PACMA31 or CCF642. In some embodiments, the anti-viral component is selected from the group consisting of: remdesivir, $\beta$-D-N$^4$-hydroxycytidine, convalescent plasma, Covid-19 monoclonal antibodies, and favipiravir. In some embodiments, the PDIA3 inhibitor is a reversible inhibitor. In another embodiment, the PDIA3 inhibitor is a selective PDIA3 inhibitor. In one embodiment, the selective PDIA3 inhibitor binds with a higher affinity to PDIA3 than PDIA1.

The disclosure, in some aspects, provides a a method of treating a human coronavirus infection, the method comprising administering to a subject in need thereof, a composition comprising a protein disulfide isomerase (PDI) inhibitor and a pharmaceutically acceptable excipient.

In some embodiments, the PDI inhibitor is a small molecule inhibitor, an anti-PDI antibody, or an inhibitory nucleic acid. In some embodiments, the inhibitory nucleic acid is a small interfering RNA (siRNA).

In some embodiments, the PDI inhibitor is a protein disulfide isomerase A3 (PDIA3) inhibitor. In some embodiments, the PDIA3 inhibitor is lead optimized compound 14 (LOC14) or variant thereof. In some embodiments, the PDIA3 inhibitor is selected from the group consisting of: PACMA31, punicalagin and CCF642.

In some embodiments, the human coronavirus is selected from the group consisting of: a severe acute respiratory syndrome (SARS) coronavirus, Middle East Respiratory Syndrome coronavirus (MERS-CoV), 229E, NL63, OC43, and HKU1.

In some embodiments, the PDIA3 inhibitor is a reversible inhibitor. In some embodiments, the PDIA3 inhibitor is a selective PDIA3 inhibitor. In some embodiments, the selective PDIA3 inhibitor binds with a higher affinity to PDIA3 than PDIA1.

Another aspect of the disclosure provides a method for identifying a human coronavirus therapeutic agent, comprising, determining a level of PDIA3 inhibition in a cell or in vitro assay in response to exposure of the PDIA3 to a putative agent, and wherein the level of PDIA3 relative to a baseline level is lower than the baseline, the putative agent is a human coronavirus therapeutic agent.

In some embodiments, the human coronavirus is selected from the group consisting of: a severe acute respiratory syndrome (SARS) coronavirus, Middle East Respiratory Syndrome coronavirus (MERS-CoV), 229E, NL63, OC43, and HKU1.

The disclosure, in another aspect, provides an anti-human coronavirus composition comprising at least one protein disulfide isomerase A3 (PDIA3) inhibitor, an anti-viral component and a pharmaceutically acceptable excipient.

In some embodiments, the PDIA3 inhibitor is lead optimized compound 14 (LOC14) or a variant thereof. In some embodiments, the PDIA3 inhibitor is PACMA31, punicalagin, or CCF642. In some embodiments, the PDIA3 inhibitor is a reversible inhibitor. In some embodiments, the PDIA3 inhibitor is a selective PDIA3 inhibitor. In some embodiments, the selective PDIA3 inhibitor binds with a higher affinity to PDIA3 than PDIA1.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways. The details of one or more embodiments of the invention are set forth in the accompanying Detailed Description, Examples, Claims, and Figures. Other features, objects, and advantages of the invention will be apparent from the description and from the claims.

BRIEF DESCRIPTION OF THE DRAWING

The accompanying drawing is not intended to be drawn to scale. In the drawing, each identical or nearly identical component that is illustrated in various figures is represented by a like numeral. For purposes of clarity, not every component may be labeled in every drawing. In the drawing.

DETAILED DESCRIPTION OF THE INVENTION

Figures 1A, 1B, 1C:
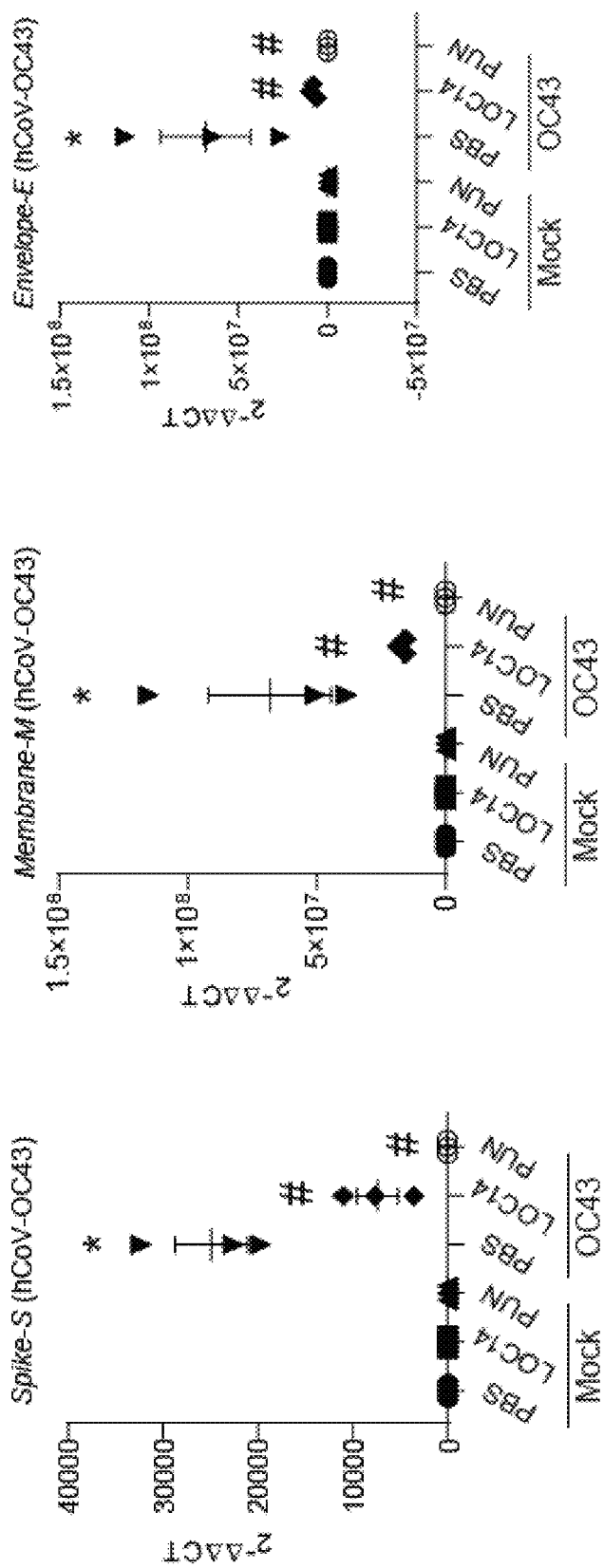
FIGS. 1A-1C are graphs showing the levels of human coronavirus OC43 (hCoV-OC43) spike protein mRNA (FIG. 1A), hCoV-OC43 membrane protein mRNA (FIG. 1B), and hCoV-OC43 envelope protein mRNA (FIG. 1C) in human bronchial epithelial cells infected with human coronavirus OC43 and then treated with a control (PBS) or PDIA3 inhibitor: LOC14 (30 μM) or punicalagin (30 μM). *$p<0.05$ compared to mock groups, #$p<0.05$ compared to OC43-PBS group by one way ANOVA.

Since the beginning of the 21st century, three coronaviruses: severe acute respiratory syndrome coronavirus 1 (SARS-CoV-1), Middle Eastern respiratory syndrome coronavirus (MERS-CoV), and SARS-CoV-2, have undergone zoonotic transmission to trigger fatal pneumonia in humans. Specifically, SARS-CoV-2-induced COVID-19 presents with symptoms of acute lung injury (ALI) and subsequent acute respiratory distress syndrome (ARDS), which accounts for the majority of the respiratory failure and mortality related to SARS-COV-2 infection. Similar pathological features have also been observed in SARS-coronavirus-1 (SARS-CoV-1), Middle Eastern Respiratory-Syndrome Coronavirus (MERS-CoV) infection, and in pandemic H1N1 (pdm-09) infected patient lungs. However, there are no available medications or vaccines for human coronaviruses, such as SARS-COV-1/2 or MERS-CoV-induced ALI-ARDS.

The present disclosure relates, in one aspect, to the discovery that protein disulfide isomerases (PDIs), specifically PDIA3, directly interact with the influenza virus and that inhibitors of PDIA3 decrease viral load and are therefore useful for therapeutic benefit against other viruses. As coronavirus (e.g., SARS-CoV-2) proteins and cytokines may be substrates for PDIs, inhibition of PDIs will similarly destabilize disulfide bonds in the viral proteins (S, M, and E) and cytokines, rendering them inactive and attenuating the spread of the virus. Specifically, SARS-CoV-2 spike (S), membrane (M), and envelope (E) proteins comprise disulfide bonds and have been found to have similarities with influenza proteins (hemagglutinin and neuraminidase) that traverse through the endoplasmic reticulum (ER) and are post-translationally modified in the ER. Prior work demonstrated that decreasing disulfide bonds in HA leads to significantly decreased viral loads and pro-inflammatory response from lung epithelial cells. Further, lung epithelial-specific deletion of PDIA3 in mice was previously found to significantly decrease viral burden and levels of inflammatory-immune markers in mouse lung, as well as significantly improved airway mechanics. PDIA3 appears to be required for effective viral pathogenesis in vivo and inhibition of PDIA3 may provide effective therapeutic benefits. Accordingly, in some aspects, the present disclosure relates to compositions and methods for treating and/or preventing coronavirus infections, such as SARS infections (e.g., SARS-CoV-2).

Recent studies have identified that a metallopeptidase angiotensin-converting enzyme 2 (ACE2) as a primary receptor for coronaviruses, including SARS-CoV-2. Furthermore, lung type 1 and 2 pneumocytes (lung epithelial cells) abundantly express ACE2, potentially making them the primary host cells for SARS-CoV infections. CoVs entry is mediated by Spike (S) protein, a surface glycoprotein on the virus that binds to epithelial cell surface receptors, including ACE2. This binding triggers endocytosis of the receptors along with the virus, and by subsequent steps, the viral nucleocapsid is released into the cytosol, where the viral RNA is replicated, and a majority of the viral proteins are translated. Among them, the S, M, and E proteins are required for viral assembly/release and re-infection. The three proteins are translated on the ER membrane ribosomes and post-translationally modified in the ER. The virions are then assembled at the ER-Golgi intermediate compartment (ERGIC). An increase in CoV-protein synthesis in the ER evokes an unfolded protein response (UPR), which subsequently facilitates folding and post-translational modifications of CoV proteins. Post-translational modifications such as disulfide bonds (—S—S—) in the S protein are critical for oligomerization, ACE2 binding, and the interaction of S and E proteins. Without wishing to be bound by theory, it is thought that protein disulfide isomerases (PDIs) are important for intra and/or intermolecular disulfide bond formation in S, M, and E proteins of SARS-CoV-2, and that inhibiting PDIs will prevent the correct folding of the viral proteins, rendering them less functional or non-functional and resulting in decreased viral burden in lung epithelial cells.

Further, SARS-CoV-2 infections have been found to induce atypical pneumonia, characterized by cough, fever, and infiltrates with a ground-glass appearance on X-ray images. Initial stages of the disease are characterized by diffuse alveolar damage (DAD), with edema, fibrin, and hyaline membrane depositions in the alveolar spaces, which is typical of acute lung injury (ALI) and acute respiratory distress syndrome (ARDS). Patients predominantly showed an acute fibrinous and organizing pneumonia pattern or a mixture of the two patterns. The longer-term disease progresses to the organizing phase of DAD and the formation of fibrous tissue. Fatal SARS-CoV-2 cases have revealed denuded airways, hemorrhage, and increased macrophage populations in the lung. During the SARS epidemic, it was noted that disease progression was unrelated to viremia but was more likely to be associated with an exuberant immune response. Likewise, initially, SARS-CoV-2 evades detection by the immune system, and then 24 to 48 hours after infection, SARS-CoV-2-induced pro-inflammatory cytokines and chemokines, including IL-6, TNFα, IL-1β, and CCL2, recruit neutrophils and cytotoxic T cells to the site of infection. However, overt recruitment of these cells, along with cytokines, can induce tissue damage, including vascular leakage, and stimulate pulmonary fibrosis. Mouse models have shown increased expression of pro-fibrotic genes, including numerous collagens. Exudates, hemorrhage, and fibrin formation are also observed in the alveolar spaces of SARS patients, as well as in animal models of disease. Prior work has demonstrated that influenza-induced increases in cytokines and chemokines such as IL-6, CXCL1/8 or CCL20 and exuberant inflammatory response and immunopathology can be decreased by inhibition or deletion of specific PDIs. Therefore, without wishing to be bound by theory, it is thought that PDI inhibition attenuate SARS-CoV-2 propagation and decreases an exuberant inflammatory response and ALI/ARDS.

SARS viruses are a species of coronaviruses that are enveloped positive-sense single-stranded RNA viruses. SARS viruses comprise a 30 kb genome, having 14 open reading frames, a 5' methylated cap, and 3' polyadenylated tail. SARS-CoV-2 is unique among SARS viruses, as it also comprises a polybasic cleavage site. The virus itself is a large pleomorphic spherical particle having projections that form a corona around the particle. The viral envelope comprises a lipid bilayer containing the S, E, and M proteins. The nucleocapsid, comprising multiple copies of a nucleocapsid (N) protein is located inside the envelope.

In some embodiments, the SARS virus may be coronavirus 1 (SARS-CoV-1) or coronavirus 2 (SARS-CoV-2). Other coronaviruses are possible and within the scope of the disclosure.

In some embodiments, the coronavirus is human coronavirus OC43 (HCoV-OC43). HCoV-OC43 is a betacoronavirus that infects humans and cattle. The virus is an enveloped, positive-sense, single stranded RNA virus, and is a virus responsible for the common cold. It is thought to have originated in rodents, and then passed through cattle as intermediate hosts. There are four genotypes (A-D), and recombinant genotype D variants are the most recent, dating back to 2004 (Lim et al., Diseases. 4(3): 26). The virus' genome is approximately 30 kb in length, comprising 11 major open reading frames (ORFs) encoding the envelope (E) protein, spike (S) protein, nucleocapsid (N) protein, and the (M) membrane protein, among others (J. Virol. 2005; 79(3): 1595-1604).

In some embodiments, the coronavirus may be HKU1-CoV, a betacoronavirus that infects the human respiratory tract, causing symptoms of the common cold, with the potential to progress to more severe pneumonia and/or bronchitis. HKU1-CoV likely originated from spillover of a rodent betacoronavirus into humans, but is now endemic in origin (Lau et al. J Clin Microbiol. 2006. 44(6):2063-2071). The HKU1-CoV is also about 30 kb long, and includes M, E, N, and S proteins (Ency. Of Virol. 2021:428-440).

In some embodiments, the coronavirus may be NL63-CoV, an alphacoronavirus that infects the human respiratory tract, particularly of children. Infection by NL63-CoV typically causes upper respiratory tract symptoms similar to the common cold, but may progress to more severe symptoms of pneumonia or bronchitis following infection of the lower respiratory tract (Abdul-Rasool et al. Open Virol J. 2010. 4:76-84). The HKU1-CoV is also about 30 kb long, and includes M, E, N, and S proteins (Ency. Of Virol. 2021:428-440).

In another embodiment, the coronavirus may be human coronavirus 229E, which infects humans and bats. It is an enveloped, positive-sense, single-stranded RNA virus. It is one of the viruses responsible for the common cold. Its genome is approximately 30,000 nucleotides long and includes spike, envelope, membrane, and nucleocapsid proteins (Korsman et al., Virology, 2012). Human coronavirus 229E is approximately 30 kb long, and includes M, E, N, and S proteins (Ency. Of Virol. 2021:428-440).

As another example, in some embodiments, the coronavirus may be Middle East Respiratory Syndrome (MERS), a betacoronavirus that infects the human respiratory tract and may be fatal. MERS-CoV is endemic in dromedary camels of East Africa and the Arabian Peninsula, and was first reported to infect humans in 2012. Though zoonotic in origin, human-to-human transmission is possible (Ramadan et al. Germs. 2019. 9(1):35-42). MERS-CoV comprises M, E, N, and S proteins (Wang et al., J Thoracic Dis., 10(19): 2018).

Protein disulfide isomerases (PDIs) are a family of redox chaperones that catalyze formation or isomerization of disulfide bonds in proteins. PDIA3 is required for the efficient folding of certain proteins, such as influenza hemagglutinin (HA), a major surface protein of the influenza A virus, in vitro (Wang et al., 2008, J. Biol. Chem.; Daniels et al., 2003, Mol. Cell; Solda et al., 2006, J. Biol. Chem.). Without wishing to be bound by theory, it is thought that SARS-CoV proteins (S, M, and E) are post-translationally modified in the ER and therefore, may also require PDIs to fold and function properly, similar to the influenza HA protein. Without wishing to be bound by theory, it is thought that the SARS infection results in ER stress and the production of unfolded protein response (UPR), leading to an increase in PDIs and resulting in increased viral load. Therefore, lowering levels of PDIs such as PDIA3 (e.g., via an inhibitory composition) may have a beneficial therapeutic effect with respect to SARS. Accordingly, in some aspects, the disclosure provides a composition comprising PDI inhibitors (e.g., PDIA3 inhibitors) for the treatment of SARS (e.g., SARS-CoV-2).

A number of PDI inhibitors are known in the art. PDI inhibitors may small molecules. PDI inhibitors may be small molecules, such as LOC14, 16F16, CCF642, P1, and PACMA31. Variants of such small molecules are also contemplated by the disclosure, for example N-oxide, crystalline form, or hydrate of the small molecule.

A PDIA3 inhibitor, in some embodiments, refers to a compound such as a small molecule, peptide or nucleic acid that reduces the level of PDIA3 expression relative to a baseline level, such as a level prior to treatment with the compound. In some embodiments the PDIA3 inhibitor is a small molecule inhibitor such as a reversible small molecule inhibitor. In some embodiments the PDIA3 inhibitor is a small molecule inhibitor such as LOC14 or variants thereof. LOC14 has the following structure:

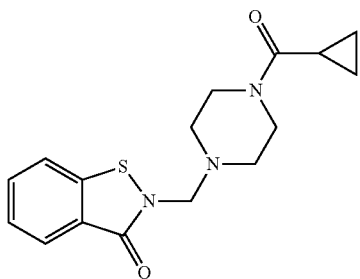 [SMILES: O=C(C1CC1)N1CCN(Cn2sc3ccccc3c2=O)CC1]

or an N-oxide, crystalline form, hydrate thereof, or a pharmaceutically acceptable salt thereof.

Variants of LOC14 are known in the art and include, for instance, analogs of LOC14 described in US Patent Application 2018/0092908, which is herein incorporated by reference.

In other embodiments the inhibitor is selected from the following compounds:

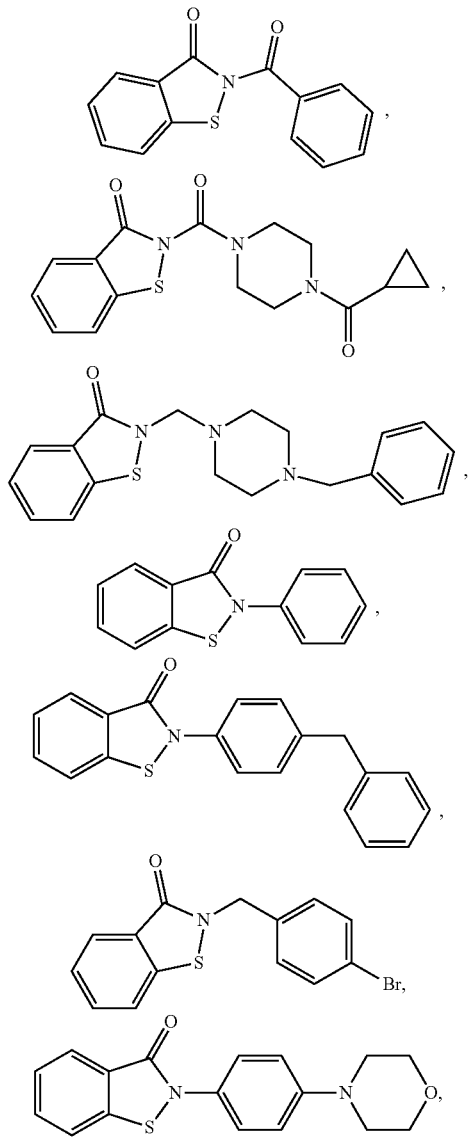

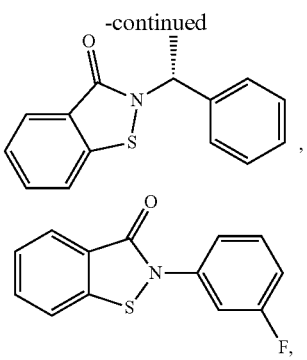

or an N-oxide, crystalline form, hydrate thereof, or a pharmaceutically acceptable salt thereof.

As used herein, "N-oxide" refers to a compound containing an N—O bond with three additional hydrogen and/or side chains attached to the N, resulting in a positive charge on the N. N-oxides of the PDI inhibitors may be synthesized by oxidation procedures known to those in the art (see, e.g., Brougham et al. (Synthesis, 1015-1017, 1987); U.S. Patent Publication No. 20070275977; S. L. Jain, J. K. Joseph, B. Sain, Synlett, 2006, 2661-2663; A. McKillop, D. Kemp, Tetrahedron, 1989, 45, 3299-3306; R. S. Varma, K. P. Naicker, Org. Lett., 1999, 1, 189-191; and N. K. Jana, J. G. Verkade, Org. Lett., 2003, 5, 3787-3790).

In other embodiments the PDIA3 inhibitor is a thiazolide compound, such as nitazoxanide or tizoxanide. In some embodiments the PDIA3 inhibitor is not a thiazolide compound.

In other embodiments the PDIA3 inhibitor is a compound of the following formula:

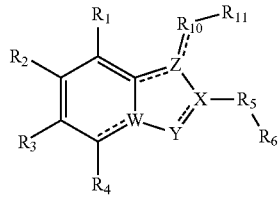

wherein a dashed line indicates the presence of an optional double bond, wherein W, X, Y and Z are independently selected from the group consisting of C, N, S and O, wherein $R_1$, $R_2$, $R_3$, and $R_4$ are independently selected from the group consisting of H, D, O, halo, $C_{1-6}$ alkyl, $C_{1-6}$ alkyl-aryl, $C_{1-6}$ alkyl-heteroaryl, $C_{1-6}$ alkenyl, $C_{1-6}$ alkenyl-aryl, and $C_{1-6}$ alkenyl-heteroaryl, wherein the $C_{1-6}$ alkyl, $C_{1-6}$ alkyl-aryl, $C_{1-6}$ alkyl-heteroaryl, $C_{1-6}$ alkenyl, $C_{1-6}$ alkenyl-aryl, and $C_{1-6}$ alkenyl-heteroaryl may be optionally substituted with an atom or a group selected from the group consisting of halo, $C_{1-4}$ alkyl, $CF_3$, and combinations thereof, wherein $R_5$, $R_6$, $R_7$, $R_8$ and $R_{10}$ are independently selected from the group consisting of no atom, NR, N(R)C(O), C(O)NR, O, C(O), C(O)O, OC(O); N(R)SO2, SO2N(R), S, SO, SO2, -(optionally substituted $C_{1-6}$ alkyl), -(optionally substituted mono- or polycyclic group containing 3 to 20 carbon atoms and optionally 1 to 4 heteroatoms selected from O, N and S), —$C_{1-4}$ alkyl-(optionally substituted mono- or polycyclic group containing 3 to 20 carbon atoms and optionally 1 to 4 heteroatoms selected from O, N and S), wherein $R_9$ and $R_{11}$ are independently selected from the group consisting of H, NR, N(R)C(O), C(O)NR, O, C(O), C(O)O, OC(O); N(R)SO2, SO2N(R), S, SO, SO2, -(optionally substituted $C_{1-6}$ alkyl), -(optionally substituted mono- or polycyclic group containing 3 to 20 carbon atoms and optionally 1 to 4 heteroatoms selected from O, N and S), —$C_{1-4}$ alkyl-(optionally substituted mono- or polycyclic group containing 3 to 20 carbon atoms and optionally 1 to 4 heteroatoms selected from O, N and S), wherein R is selected from the group consisting of H, D, O, halo, $C_{1-6}$ alkyl, $C_{1-6}$alkyl-aryl, $C_{1-6}$ alkyl-heteroaryl, $C_{1-6}$ alkenyl, $C_{1-6}$ alkenyl-aryl, and $C_{1-6}$ alkenyl-heteroaryl, wherein the $C_{1-6}$ alkyl, $C_{1-6}$alkyl-aryl, $C_{1-6}$ alkyl-heteroaryl, $C_{1-6}$alkenyl, $C_{1-6}$alkenyl-aryl, and $C_{1-6}$ alkenyl-heteroaryl may be optionally substituted with an atom or a group selected from the group consisting of halo, $C_{1-4}$ alkyl, $CF_3$, and combinations thereof, or an N-oxide, crystalline form, hydrate thereof, or a pharmaceutically acceptable salt thereof.

As used herein, "crystalline form" means the crystal structure of a compound. Compounds may exist in more than one crystalline form, and may have different structural, physical, pharmacological, and/or chemical characteristics. Various crystalline forms may be generating using varied nucleation, growth kinetics, agglomeration, and breakage. Nucleation occurs when the phase-transition energy barrier is overcome, allowing a particle to form from a supersaturated solution. Crystal growth is caused by the deposition of the chemical compound on an existing surface of the crystal, resulting in the enlargement of crystal particles. The relative rate of nucleation and growth determine the size distribution of the crystals that are formed. The thermodynamic driving force for both nucleation and growth is supersaturation, which is defined as the deviation from thermodynamic equilibrium. Agglomeration results when two or more particles (e.g., crystals) stick together, generating a larger crystalline structure.

As used herein, "hydrate" refers to a compound that contains water molecules in a definite ratio in which water forms an integral part of the crystalline structure of the compound. Synthesis of hydrates is well known in the art, for example, spontaneous absorption of water from the air, or through contact with water. In other instances, hydrates are made by changes in temperature or pressure. Additionally, the compounds of the present invention as well as their salts may contain, e.g., when isolated in crystalline form, varying amounts of solvents, such as water. All hydrates of the compounds and all hydrates of salts of the compounds are included within the scope of the disclosure.

Lead optimized compound 14 (LOC14), 2-[[4-(cyclopropylcarbonyl)-1-piperazinyl]methyl]-1,2-benzisothiazol-3 (2H)-one, is a reversible, high affinity protein disulfide isomerase modulator. It has been found to bind to PDI adjacent to its active site, forcing PDI to adopt an oxidized conformation and suppressing its activity (Kaplan et al., PNAS, 2015, 112(17):E2245-52).

In some embodiments, the PDI inhibitor is a flavonoid, such as hyperosin, isoquercetin, quercetin-3-glucuronide, quercetin-3-rutinoside, or datiscin (Jasuja et al., J Clin Invest. 212 June 1; 122(6): 2104-2113). In some embodiments the PDI inhibitor is juniferdin (Khan et al., ACS Chem Biol., 2011 Mar. 18; 6(3):245-51). In some embodiments, the PDI inhibitor is selected from the group consisting of: 16F16, PACMA31, epigallocatechin-3-gallate and nitazoxanide (Kim et al., Virus Res. 2018 Mar. 2; 247: 26-33).

In some embodiments, the PDIA3 inhibitor is an ellagitannin, such as punicalagin (Giamogante et al., Biochimie. 2018 April; 147: 122-129).

In some embodiments, the PDI inhibitor is an antibody or an inhibitory nucleic acid. Anti-PDI antibodies are antibodies which bind specifically with a PDI and inhibit its isomerase activity. Anti-PDI antibodies are known in commercially available from companies such as abcam, Invitrogen, Novus Biologicals, and Cell Signaling Technologies.

In some embodiments, the PDI inhibitor is an inhibitor nucleic acid, such as a small interfering nucleic acid (siNA). Examples of siNAs include: microRNA (miRNA), small interfering RNA (siRNA), double-stranded RNA (dsRNA), and short hairpin RNA (shRNA) molecules. An siNA useful in the invention can be unmodified or chemically-modified. An siNA of the instant invention can be chemically synthesized, expressed from a vector or enzymatically synthesized. Such methods are well known in the art. In one embodiment, one of the strands of the double-stranded siNA molecule comprises a nucleotide sequence that is complementary to a nucleotide sequence of a target RNA or a portion thereof, and the second strand of the double-stranded siNA molecule comprises a nucleotide sequence identical to the nucleotide sequence or a portion thereof of the targeted RNA. In another embodiment, one of the strands of the double-stranded siNA molecule comprises a nucleotide sequence that is substantially complementary to a nucleotide sequence of a target RNA or a portion thereof, and the second strand of the double-stranded siNA molecule comprises a nucleotide sequence substantially similar to the nucleotide sequence or a portion thereof of the target RNA. In another embodiment, each strand of the siNA molecule comprises about 19 to about 23 nucleotides, and each strand comprises at least about 19 nucleotides that are complementary to the nucleotides of the other strand.

Other inhibitor molecules that can be used include ribozymes, peptides, DNAzymes, peptide nucleic acids (PNAs), triple helix forming oligonucleotides, and aptamers and modified form(s) thereof directed to sequences in gene(s), RNA transcripts, or proteins.

As used herein, the term "treating" or "treatment" refers to the application or administration of a composition including one or more active agents to a subject, who has a target disease or disorder, a symptom of the disease/disorder, or a predisposition toward the disease/disorder, with the purpose to prevent, cure, heal, alleviate, relieve, alter, remedy, ameliorate, improve, or affect the disorder, the symptom of the disease, or the predisposition toward the disease or disorder.

Alleviating a target disease/disorder includes delaying the development or progression of the disease, or reducing disease severity or prolonging survival. Alleviating the disease or prolonging survival does not necessarily require curative results. As used therein, "delaying" the development of a target disease or disorder means to defer, hinder, slow, retard, stabilize, and/or postpone progression of the disease. This delay can be of varying lengths of time, depending on the history of the disease and/or individuals being treated. A method that "delays" or alleviates the development of a disease, or delays the onset of the disease, is a method that reduces probability of developing one or more symptoms of the disease in a given time frame and/or reduces extent of the symptoms in a given time frame, when compared to not using the method. Such comparisons are typically based on clinical studies, using a number of subjects sufficient to give a statistically significant result.

"Development" or "progression" of a disease means initial manifestations and/or ensuing progression of the disease. Development of the disease can be detectable and assessed using standard clinical techniques as well known in the art. However, development also refers to progression that may be undetectable. For purpose of this disclosure, development or progression refers to the biological course of the symptoms. "Development" includes occurrence, recurrence, and onset. As used herein "onset" or "occurrence" of a target disease or disorder includes initial onset and/or recurrence.

In some embodiments, the compositions described herein are administered to a subject in need of the treatment at an amount sufficient to inhibit the bioactivity of PDIA3 by at least 20% (e.g., 30%, 40%, 50%, 60%, 70%, 80%, 90% or greater) in vivo. In other embodiments, the compositions are administered in an amount effective for reducing the bioactivity level of PDIA3 by at least 20% (e.g., 30%, 40%, 50%, 60%, 70%, 80%, 90% or greater).

Conventional methods, known to those of ordinary skill in the art of medicine, can be used to administer the pharmaceutical composition to the subject, depending upon the type of disease to be treated or the site of the disease. This composition can also be administered via other conventional routes, e.g., administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques. In addition, it can be administered to the subject via injectable depot routes of administration such as using 1-, 3-, or 6-month depot injectable or biodegradable materials and methods. In some examples, the pharmaceutical composition is administered intraocularly or intravitreally.

Injectable compositions may contain various carriers such as vegetable oils, dimethylactamide, dimethyformamide, ethyl lactate, ethyl carbonate, isopropyl myristate, ethanol, and polyols (glycerol, propylene glycol, liquid polyethylene glycol, and the like). For intravenous injection, water soluble antibodies can be administered by the drip method, whereby a pharmaceutical formulation containing the PDI inhibitor and a physiologically acceptable excipient is infused. Physiologically acceptable excipients may include, for example, 5% dextrose, 0.9% saline, Ringer's solution or other suitable excipients. Intramuscular preparations, e.g., a sterile formulation of a suitable soluble salt form of the PDI inhibitor, can be dissolved and administered in a pharmaceutical excipient such as Water-for-Injection, 0.9% saline, or 5% glucose solution.

In one embodiment, a composition is administered via site-specific or targeted local delivery techniques. Examples of site-specific or targeted local delivery techniques include various implantable depot sources of the PDI inhibitor or local delivery catheters, such as infusion catheters, an indwelling catheter, or a needle catheter, synthetic grafts, adventitial wraps, shunts and stents or other implantable devices, site specific carriers, direct injection, or direct application. See, e.g., PCT Publication No. WO 00/53211 and U.S. Pat. No. 5,981,568.

The particular dosage regimen, i.e., dose, timing and repetition, used in the method described herein will depend on the particular subject and that subject's medical history.

In some embodiments, more than one composition, or a combination of a composition described herein and another suitable therapeutic agent, may be administered to a subject in need of the treatment. The composition described herein can also be used in conjunction with other agents that serve to enhance and/or complement the effectiveness of the agents.

Examples of secondary suitable therapeutic agents include anti-viral agents, such as remdesivir, β-D-N⁴-hydroxycytidine, convalescent plasma, Covid-19 monoclonal antibodies, and favipiravir.

Treatment efficacy for a target disease/disorder can be assessed by methods well-known in the art.

Any of the anti-SARS compositions described herein may be utilized in conjunction with other types of therapy for SARS or other infectious diseases, such as surgery, gene therapy, or in conjunction with other types of therapy for downstream effects of SARS infections such as rest, fluids, pain medication, and so forth. Such therapies can be administered simultaneously or sequentially (in any order) with the therapy according to the present disclosure.

When co-administered with an additional therapeutic agent, suitable therapeutically effective dosages for each agent may be lowered due to the additive action or synergy.

The compositions described herein can be mixed with a pharmaceutically acceptable carrier (excipient) to form a pharmaceutical composition for use in treating a target disease. "Acceptable" means that the carrier must be compatible with the active ingredient of the composition (and preferably, capable of stabilizing the active ingredient) and not deleterious to the subject to be treated. Pharmaceutically acceptable excipients (carriers) including buffers, which are well known in the art. See, e.g., Remington: The Science and Practice of Pharmacy 20th Ed. (2000) Lippincott Williams and Wilkins, Ed. K. E. Hoover.

The pharmaceutical compositions to be used in the present methods can comprise pharmaceutically acceptable carriers, excipients, or stabilizers in the form of lyophilized formulations or aqueous solutions. (Remington: The Science and Practice of Pharmacy 20th Ed. (2000) Lippincott Williams and Wilkins, Ed. K. E. Hoover). Acceptable carriers, excipients, or stabilizers are nontoxic to recipients at the dosages and concentrations used, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

In some examples, the pharmaceutical composition described herein comprises liposomes containing the PDI inhibitors which can be prepared by methods known in the art, such as described in Epstein, et al., *Proc. Natl. Acad. Sci. USA* 82:3688 (1985); Hwang, et al., *Proc. Natl. Acad. Sci. USA* 77:4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

The PDI inhibitors may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are known in the art, see, e.g., Remington, The Science and Practice of Pharmacy 20th Ed. Mack Publishing (2000).

In other examples, the pharmaceutical composition described herein can be formulated in sustained-release format. Suitable examples of sustained-release preparations include semipermeable matrices of solid hydrophobic polymers containing the PDI inhibitor, which matrices are in the form of shaped articles, e.g. films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(-)-3-hydroxybutyric acid.

The pharmaceutical compositions to be used for in vivo administration must be sterile. This is readily accomplished by, for example, filtration through sterile filtration membranes. Therapeutic compositions are generally placed into a container having a sterile access port, for example, an intravenous solution bag or vial having a stopper pierceable by a hypodermic injection needle.

The pharmaceutical compositions described herein can be in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient can be mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

Suitable surface-active agents include, in particular, non-ionic agents, such as polyoxyethylenesorbitans (e.g., Tween™ 20, 40, 60, 80 or 85) and other sorbitans (e.g., Span™ 20, 40, 60, 80 or 85). Compositions with a surface-active agent will conveniently comprise between 0.05 and 5% surface-active agent, and can be between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g., soybean oil, safflower oil, cottonseed oil, sesame oil, corn oil or almond oil) and an emulsion formed upon mixing with a phospholipid (e.g. egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion can comprise fat droplets between 0.1 and 1.0.im, particularly 0.1 and 0.5.im, and have a pH in the range of 5.5 to 8.0.

The emulsion compositions can be those prepared by mixing a PDI inhibitor with Intralipid™ or the components thereof (soybean oil, egg phospholipids, glycerol and water).

Pharmaceutical compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect.

Compositions in preferably sterile pharmaceutically acceptable solvents may be nebulized by use of gases. Nebulized solutions may be breathed directly from the nebulizing device or the nebulizing device may be attached to a face mask, tent or intermittent positive pressure breathing machine. Solution, suspension or powder compositions may be administered, preferably orally or nasally, from devices which deliver the formulation in an appropriate manner.

To practice the method disclosed herein, an effective amount of the pharmaceutical composition described herein can be administered to a subject (e.g., a human) in need of the treatment via a suitable route, such as intravenous administration, e.g., as a bolus or by continuous infusion over a period of time, by intramuscular, intraperitoneal, intracerebrospinal, subcutaneous, intra-articular, intrasynovial, intrathecal, oral, inhalation or topical routes. Commercially available nebulizers for liquid formulations, including jet nebulizers and ultrasonic nebulizers are useful for administration. Liquid formulations can be directly nebulized and lyophilized powder can be nebulized after reconstitution. Alternatively, the antibodies as described herein can be aerosolized using a fluorocarbon formulation and a metered dose inhaler, or inhaled as a lyophilized and milled powder.

The subject to be treated by the methods described herein can be a mammal, more preferably a human. Mammals include, but are not limited to, farm animals, sport animals, pets, primates, horses, dogs, cats, mice and rats. A human subject who needs the treatment may be a human patient having, at risk for, or suspected of having a target disease/disorder, such as a SARS infection (e.g., COVID-19).

A subject suspected of having any of such target disease/disorder might show one or more symptoms of the disease/disorder or alternatively may test positive for the infectious agent. A subject at risk for the disease/disorder can be a subject having one or more of the risk factors for that disease/disorder or exposed to the infectious agent.

As used herein, "an effective amount" refers to the amount of each active agent required to confer therapeutic effect on the subject, either alone or in combination with one or more other active agents. In some embodiments, the therapeutic effect is reduced PDI bioactivity. Determination of whether an amount of the composition achieved the therapeutic effect would be evident to one of skill in the art. Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment.

Empirical considerations, such as the half-life, generally will contribute to the determination of the dosage. Frequency of administration may be determined and adjusted over the course of therapy, and is generally, but not necessarily, based on treatment and/or suppression and/or amelioration and/or delay of a target disease/disorder. Alternatively, sustained continuous release formulations of a PDI inhibitor may be appropriate. Various formulations and devices for achieving sustained release are known in the art.

In one example, dosages for a PDI inhibitor as described herein may be determined empirically in individuals who have been given one or more administration(s) of the PDI inhibitor.

Generally, for administration of any of the PDI inhibitors described herein, an initial candidate dosage can be about 2 mg/kg. For the purpose of the present disclosure, a typical daily dosage might range from about any of 0.1 mg/kg to 3 mg/kg to 30 mg/kg to 300 mg/kg to 3 mg/kg, to 30 mg/kg to 100 mg/kg or more, depending on the factors mentioned above. For repeated administrations over several days or longer, depending on the condition, the treatment is sustained until a desired suppression of symptoms occurs or until sufficient therapeutic levels are achieved to alleviate a target disease or disorder, or a symptom thereof. An exemplary dosing regimen comprises administering an initial dose of about 2 mg/kg, followed by a weekly maintenance dose of about 1 mg/kg of the PDI inhibitor, or followed by a maintenance dose of about 1 mg/kg every other week. However, other dosage regimens may be useful, depending on the pattern of pharmacokinetic decay that the practitioner wishes to achieve. For example, dosing from one-four times a week is contemplated. In some embodiments, dosing ranging from about 3 μg/mg to about 2 mg/kg (such as about 3 μg/mg, about 10 μg/mg, about 30 μg/mg, about 100 μg/mg, about 300 μg/mg, about 1 mg/kg, and about 2 mg/kg) may be used. In some embodiments, dosing frequency is once every week, every 2 weeks, every 4 weeks, every 5 weeks, every 6 weeks, every 7 weeks, every 8 weeks, every 9 weeks, or every 10 weeks; or once every month, every 2 months, or every 3 months, or longer. The progress of this therapy is easily monitored by conventional techniques and assays. The dosing regimen (including the PDI inhibitor used) can vary over time.

In some embodiments, for an adult patient of normal weight, doses ranging from about 0.3 to 5.00 mg/kg may be administered. In some examples, the dosage of the PDI inhibitor described herein can be 10 mg/kg. The particular dosage regimen, i.e., dose, timing and repetition, will depend on the particular individual and that individual's medical history, as well as the properties of the individual agents (such as the half-life of the agent, and other considerations well known in the art).

For the purpose of the present disclosure, the appropriate dosage of a PDI inhibitor as described herein will depend on the specific PDI inhibitor, PDI inhibitors, and/or other therapeutic agents (or compositions thereof) employed, the type and severity of the disease/disorder, whether the PDI inhibitor is administered for preventive or therapeutic purposes, previous therapy, the patient's clinical history and response to the antagonist, and the discretion of the attending physician. Typically, the clinician will administer a composition until a dosage is reached that achieves the desired result. In some embodiments, the desired result is a reduction in viral load. Methods of determining whether a dosage resulted in the desired result would be evident to one of skill in the art. Administration of one or more PDI inhibitors can be continuous or intermittent, depending, for example, upon the recipient's physiological condition, whether the purpose of the administration is therapeutic or prophylactic, and other factors known to skilled practitioners. The administration of a PDI inhibitor may be essentially continuous over a preselected period of time or may be in a series of spaced dose, e.g., either before, during, or after developing a target disease or disorder.

The present disclosure also provides kits for use in treating or alleviating SARS (e.g., COVID-19). Such kits can include one or more containers comprising a PDI inhibitor, e.g., any of those described herein.

In some embodiments, the kit can comprise instructions for use in accordance with any of the methods described herein. The included instructions can comprise a description of administration of the PDI inhibitor, and optionally the second therapeutic agent, to treat, delay the onset, or alleviate a target disease as those described herein. The kit may further comprise a description of selecting an individual suitable for treatment based on identifying whether that individual has the target disease, e.g., applying the diagnostic method as described herein. In still other embodiments, the instructions comprise a description of administering a PDI inhibitor to an individual at risk of the target disease.

The instructions relating to the use of a PDI inhibitor generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The label or package insert indicates that the composition is used for treating, delaying the onset and/or alleviating SARS (e.g., COVID-19). Instructions may be provided for practicing any of the methods described herein.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is a PDI inhibitor as those described herein.

Kits may optionally provide additional components such as buffers and interpretive information. Normally, the kit comprises a container and a label or package insert(s) on or associated with the container. In some embodiments, the invention provides articles of manufacture comprising contents of the kits described above.

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook, et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-8) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel, et al., eds., 1987); PCR: The Polymerase Chain Reaction, (Mullis, et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995).

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

In order that the invention described herein may be more fully understood, the following examples are set forth. The examples described in this application are offered to illustrate the compounds, pharmaceutical compositions, and methods provided herein and are not to be construed in any way as limiting their scope.

Example 1. Interaction of SARS-CoV-2 S, M, and E Proteins with Lung Epithelial Cell PDIs The interaction of SARS-CoV-2 S, M, and E proteins with lung epithelial cell PDIs is examined. SARS-CoV proteins S, M, and E are post-translationally modified in the ER. The infection of SARS-CoV also induces unfolded protein response (UPR) in cells, which may aids in viral protein folding and activity. Recent reports suggest that disulfide bonds of the SARS-CoV proteins (e.g., S and M) are important determinants of their structure and function.

Human bronchiolar epithelial cells are infected with SARS-CoV-2 (WA1-USA/2020 strain obtained from BEI resources), and viral proteins, S, M, and E are immunoprecipitated (IP) at various time points ranging from 3 hours to 24 hours using specific antibodies for the respective proteins. Subsequently, Mass Spectrometric analysis of the immunoprecipitated proteins is conducted to identify specific PDIs interacting with SARS-CoV-2 S, M, and E proteins. Once PDIs interacting with viral proteins are identified, they are confirmed by Western blot analysis of the immunoprecipitated samples. Next, small interfering (si) RNA or CRISPR-Cas9 approaches are used to knock down or knock out specific PDIs. These cells along with scrambled siRNA transfected or wild type (WT) cells are infected with SARS-CoV-2 to determine whether specific PDIs are required for the processing of SARS-CoV-2 proteins. Cell lysates are analyzed for viral proteins and their disulfide status using a biotinylated cysteine derivatization method and detection by probing with streptavidin-HRP and oligomerization of viral proteins are detected by redox-based Western blots. Further, culture supernatants are collected to analyze whether a decrease in specific PDIs results in decreased production of the virus by $TCID_{50}$ assay as well as viral RNA quantitation by RT-qPCR.

While disulfide bonds are known to be crucial for secretory protein structure, stability, and function, earlier work in influenza-induced inflammatory response suggests that PDI inhibition or deletion decreases disulfide bond formation and subsequent secretion of cytokines and chemokines. SARS-CoV infection is known to produce an exuberant pro-inflammatory response, including IL6, IL8, IL10, IL1β, TNFα, CCL20, CCL2, MCP-1, and MIP-1. All these proteins have disulfide bonds, traverse through the ER, and require post-translational modifications such as glycosylation that are critical for their secretion and activity. To understand the significance of PDIs and disulfide bonds in SARS-CoV-2-induced inflammatory proteins, primary human bronchial epithelial cells are infected with SARS-CoV-2 along with inhibitors of PDIs. Then subcellular fractions including cytosol, ER, and Golgi are collected by differential lysis and centrifugation and supernatants are cultured at various time points (30, 60, 120, 360 minutes, and 24 hrs). During the lysis of subcellular fractions, sulfhydryl (—SH) groups of the proteins are labeled with MPB. The lysed fractions will be subjected to immunoprecipitation using various cytokine and chemokine antibodies. The subsequent Western blot analysis and quantitation using streptavidin HRP and total levels of cytokines and chemokines is used to determine whether the ER of the PDI inhibited epithelial cells retains more of —SH (MPB labeling) compared to vehicle control-treated cells. Quantitation of culture supernatants for various cytokines and chemokines by ELISA or Quantikine analyses reveals the differences in secretion based on disulfide status. Similar experiments are repeated using SARS-CoV-2-infected HBE cells with knockdown of specific PDIs.

In this way, the impact of PDIs on disulfide bonds of SARS proteins and their activities are determined, as well as the effect of airway epithelial knockdown or inhibition of specific PDIs on SARS-CoV-2 propagation and inflammation.

Example 2: Effect of Inhibition of PDIs in Resolution of SARS-CoV-2-Induced Inflammatory Response and ALI Literature suggests that disulfide bonds are critical in SARS-CoV-2 proteins and inflammatory cytokines/chemokine structure and function. Therefore, experiments are undertaken using mouse models to determine whether inhibition of PDIs alters the disulfide bonds in the viral proteins and inflammatory cytokines/chemokines. Whether PDI inhibition decreases immunopathology and lung function is also examined.

To test the effectiveness of PDI inhibitors in a mouse model of SARS-CoV-2 infection and to decrease the systemic toxicity, K18-hACE2 mice are infected with SARS-CoV-2. Twenty-four hours later, select PDI inhibitors are administered via the oropharyngeal route every day for 5 days. The doses are calculated based on surface area of the mouse lung and the effective concentration in cell culture experiments described in Example 1.

At the end of the experiment, the effect of this treatment on inhibition of pro-inflammatory cytokine and chemokine production, inhibition of PDI activity is determined using an enzyme assay on the immunoprecipitated PDIs and SARS-CoV-2 burden using RT-qPCR assay for replicase and nucleocapsid. Based on the quantitation of these results, the effective concentration is calculated ($EC_{50}$). Next, time course experiments will be undertaken with shorter (days 1, 3, and 5 post-infection) and longer time points (days 7, 10, and 14 post-infections) to assess the impacts of PDI inhibition on SARS-CoV-2, clinical disease, immunopathology, and lung function. Briefly, groups of K18-hACE2 mice are infected with $10^3$ plaque forming units of SARS-CoV-2 with and without PDI inhibitors as described above. In addition to monitoring clinical disease throughout the experiment, four mice from each group are sacrificed on indicated days, lungs isolated, homogenized, and expression of pro- and anti-inflammatory cytokines is measured as described below. Separate set of mice are used to isolate lungs for histopathological studies on indicated days. Next, experiments with longer time points (~20-40 days) are performed to assess the impacts of PDI inhibition on SARS-CoV-2, immunopathology, and lung function.

Homogenized lung samples are analyzed for alterations in PDI expression by Western blots and RT-qPCR. The SARS-CoV-2 burden is analyzed using RT-qPCR for viral replicase and nucleocapsid mRNAs, and a re-infection assay is performed in HBE cells using bronchoalveolar lavage of infected mice. The expression of cytokines and chemokines (e.g., IL-1β, IL-18, IFN-α/β/γ, IL-6, CXCL1, G-CSF, and CCL20) is determined with multiplex cytokine assays and RT-qPCR. Paraffin-embedded sections are stained for epithelial cell-specific markers (EpCAM or E-cadherin or CC10), PDIs, and viral proteins. Lung tissue is also quantitated for fibrin exudates by immunohistochemistry (IHC) and Western blot analysis for fibrin and PAI-I to assess lung injury. Apoptosis of epithelial cells is measured by active caspase-3 staining of the lung tissue and enzyme activity measurement from the lung lysates. The lung samples from all the above experiments are analyzed for alterations in disulfides (—S—S—) of cytokines/chemokines, SARS-CoV-2 S, M, and E. In addition to the above analyses, the impact of inhibition of PDIs in SARS-CoV-2 infected mice is determined using oxygen saturation measurements (PhysioSuite-Pulse Oximetry, Kent Scientific), including end-tidal $CO_2$ measurements, in the above experiments.

Results are analyzed by ANOVA, followed by Tukey's multiple comparison test. Student's t-test is used where appropriate. Three independent scientists blinded for the experiments score the staining. Scores are pooled and analyzed using Kruskal-Wallis test and Dunn's multiple comparison tests. Cell culture assays are performed in triplicate. Cell culture experiments are analyzed separately, and if consistent, a combined analysis is performed. The experiments will be conducted in two cohorts of n=5 or n=3 to reach the required number of animals to reach statistical significance. Mouse experiments are repeated for reproducibility.

Example 3. Attenuation of Human Coronavirus (hCOV)-OC43 Replication by PDIA3 Inhibitors Human bronchial epithelial cells were infected with 0.25 plaque-forming units (pfu) of human coronavirus (hCOV)-OC43 and then treated with PBS (control) or LOC13 (30 μM) or punicalagin (30 μM), two exemplary PDIA3 inhibitors. The resulting cell lysates were prepared for RNA extraction. Spike, membrane, and envelope mRNA were analyzed from the lysates using quantitative RT-qPCR (with SYBR-Green). The data is shown in FIGS. 1A-1C, and demonstrates that treatment with PDIA3 inhibitors significantly decreased the levels of all three proteins (p<0.05 compared to the PBS group by one way ANOVA).

REFERENCES

1. Fung T S, Liu D X. Post-translational modifications of coronavirus proteins: roles and function. Future Virol. 2018; 13(6):405-30. Epub 2018 Jun. 1. doi: 10.2217/fvl-2018-0008. PubMed PMID: 32201497; PMCID: PMC7080180.
2. Fenouillet E, Barbouche R, Jones I M. Cell entry by enveloped viruses: redox considerations for HIV and SARS-coronavirus. Antioxid Redox Signal. 2007; 9(8): 1009-34. Epub 2007 Jun. 15. doi: 10.1089/ars.2007.1639. PubMed PMID: 17567241.
3. Roberson E C, Tully J E, Guala A S, Reiss J N, Godburn K E, Pociask D A, Alcorn J F, Riches D W, Dienz O, Janssen-Heininger Y M, Anathy V. Influenza induces endoplasmic reticulum stress, caspase-12-dependent apoptosis, and c-Jun N-terminal kinase-mediated transforming growth factor-beta release in lung epithelial cells. Am J Respir Cell Mol Biol. 2012; 46(5):573-81. Epub 2011 Jul. 30. doi: 10.1165/rcmb.2010-0460OC. PubMed PMID: 21799120; PMCID: PMC3359902.
4. Chamberlain N, Korwin-Mihavics B R, Nakada E M, Bruno S R, Heppner D E, Chapman D G, Hoffman S M, van der Vliet A, Suratt B T, Dienz O, Alcorn J F, Anathy V. Lung epithelial protein disulfide isomerase A3 (PDIA3) plays an important role in influenza infection, inflammation, and airway mechanics. Redox Biol. 2019;

22:101129. Epub 2019 Feb. 9. doi: 10.1016/j.redox.2019.101129. PubMed PMID: 30735910; PMCID: PMC6365984.
5. Li S, Yuan L, Dai G, Chen R A, Liu D X, Fung T S. Regulation of the E R Stress Response by the Ion Channel Activity of the Infectious Bronchitis Coronavirus Envelope Protein Modulates Virion Release, Apoptosis, Viral Fitness, and Pathogenesis. Front Microbiol. 2019; 10:3022. Epub 2020 Feb. 11. doi: 10.3389/fmicb.2019.03022. PubMed PMID: 32038520; PMCID: PMC6992538.
6. Sanders J M, Monogue M L, Jodlowski T Z, Cutrell J B. Pharmacologic Treatments for Coronavirus Disease 2019 (COVID-19): A Review. JAMA. 2020. Epub 2020 Apr. 14. doi: 10.1001/jama.2020.6019. PubMed PMID: 32282022.
7. Bar-On Y M, Flamholz A, Phillips R, Milo R. SARS-CoV-2 (COVID-19) by the numbers. Elife. 2020; 9. Epub 2020 Apr. 2. doi: 10.7554/eLife.57309. PubMed PMID: 32228860.
8. Gralinski L E, Baric R S. Molecular pathology of emerging coronavirus infections. J Pathol. 2015; 235(2):185-95. Epub 2014 Oct. 2. doi: 10.1002/path.4454. PubMed PMID: 25270030; PMCID: PMC4267971.
9. Gill J R, Sheng Z M, Ely S F, Guinee D G, Beasley M B, Suh J, Deshpande C, Mollura D J, Morens D M, Bray M, Travis W D, Taubenberger J K. Pulmonary pathologic findings of fatal 2009 pandemic influenza A/H1N1 viral infections. Arch Pathol Lab Med. 2010; 134(2):235-43. Epub 2010 Feb. 4. doi: 10.1043/1543-2165-134.2.235. PubMed PMID: 20121613; PMCID: PMC2819217.
10. Fung T S, Liu D X. Human Coronavirus: Host-Pathogen Interaction. Annu Rev Microbiol. 2019; 73:529-57. Epub 2019 Jun. 22. doi: 10.1146/annurev-micro-020518-115759. PubMed PMID: 31226023.
11. Drosten C, Gunther S, Preiser W, van der Werf S, Brodt H R, Becker S, Rabenau H, Panning M, Kolesnikova L, Fouchier R A, Berger A, Burguiere A M, Cinatl J, Eickmann M, Escriou N, Grywna K, Kramme S, Manuguerra J C, Muller S, Rickerts V, Sturmer M, Vieth S, Klenk H D, Osterhaus A D, Schmitz H, Doerr H W. Identification of a novel coronavirus in patients with severe acute respiratory syndrome. N Engl J Med. 2003; 348(20): 1967-76. Epub 2003 Apr. 12. doi: 10.1056/NEJMoa030747. PubMed PMID: 12690091.
12. Zaki A M, van Boheemen S, Bestebroer T M, Osterhaus A D, Fouchier R A. Isolation of a novel coronavirus from a man with pneumonia in Saudi Arabia. N Engl J Med. 2012; 367(19):1814-20. Epub 2012 Oct. 19. doi: 10.1056/NEJMoa1211721. PubMed PMID: 23075143.
13. Zhou P, Yang X L, Wang X G, Hu B, Zhang L, Zhang W, Si H R, Zhu Y, Li B, Huang C L, Chen H D, Chen J, Luo Y, Guo H, Jiang R D, Liu M Q, Chen Y, Shen X R, Wang X, Zheng X S, Zhao K, Chen Q J, Deng F, Liu L L, Yan B, Zhan F X, Wang Y Y, Xiao G F, Shi Z L. A pneumonia outbreak associated with a new coronavirus of probable bat origin. Nature. 2020; 579(7798):270-3. Epub 2020 Feb. 6. doi: 10.1038/s41586-020-2012-7. PubMed PMID: 32015507; PMCID: PMC7095418.
14. Hoffmann M, Kleine-Weber H, Schroeder S, Kruger N, Herrler T, Erichsen S, Schiergens T S, Herrler G, Wu N H, Nitsche A, Muller M A, Drosten C, Pohlmann S. SARS-CoV-2 Cell Entry Depends on ACE2 and TMPRSS2 and Is Blocked by a Clinically Proven Protease Inhibitor. Cell. 2020; 181(2):271-80 e8. Epub 2020 Mar. 7. doi: 10.1016/j.cell.2020.02.052. PubMed PMID: 32142651; PMCID: PMC7102627.
15. Hamming I, Timens W, Bulthuis M L, Lely A T, Navis G, van Goor H. Tissue distribution of ACE2 protein, the functional receptor for SARS coronavirus. A first step in understanding SARS pathogenesis. J Pathol. 2004; 203 (2):631-7. Epub 2004 May 14. doi: 10.1002/path.1570. PubMed PMID: 15141377.
16. Masters P S. The molecular biology of coronaviruses. Adv Virus Res. 2006; 66:193-292. Epub 2006 Aug. 1. doi: 10.1016/S0065-3527(06)66005-3. PubMed PMID: 16877062; PMCID: PMC7112330.
17. Klumperman J, Locker J K, Meijer A, Horzinek M C, Geuze H J, Rottier P J. Coronavirus M proteins accumulate in the Golgi complex beyond the site of virion budding. J Virol. 1994; 68(10):6523-34. Epub 1994 Oct. 1. PubMed PMID: 8083990; PMCID: PMC237073.
18. Sung S C, Chao C Y, Jeng K S, Yang J Y, Lai M M. The 8ab protein of SARS-CoV is a luminal E R membrane-associated protein and induces the activation of ATF6. Virology. 2009; 387(2):402-13. Epub 2009 Mar. 24. doi: 10.1016/j.virol.2009.02.021. PubMed PMID: 19304306; PMCID: PMC7103415.
19. Siu K L, Chan C P, Kok K H, Woo P C, Jin D Y. Comparative analysis of the activation of unfolded protein response by spike proteins of severe acute respiratory syndrome coronavirus and human coronavirus HKU1. Cell Biosci. 2014; 4(1):3. Epub 2014 Jan. 15. doi: 10.1186/2045-3701-4-3. PubMed PMID: 24410900; PMCID: PMC3930072.
20. Tang B S, Chan K H, Cheng V C, Woo P C, Lau S K, Lam C C, Chan T L, Wu A K, Hung I F, Leung S Y, Yuen K Y. Comparative host gene transcription by microarray analysis early after infection of the Huh7 cell line by severe acute respiratory syndrome coronavirus and human coronavirus 229E. J Virol. 2005; 79(10):6180-93. Epub 2005 Apr. 29. doi: 10.1128/JVI.79.10.6180-6193.2005. PubMed PMID: 15858003; PMCID: PMC1091719.
21. Fukushi M, Yoshinaka Y, Matsuoka Y, Hatakeyama S, Ishizaka Y, Kirikae T, Sasazuki T, Miyoshi-Akiyama T. Monitoring of S protein maturation in the endoplasmic reticulum by calnexin is important for the infectivity of severe acute respiratory syndrome coronavirus. J Virol. 2012; 86(21):11745-53. Epub 2012 Aug. 24. doi: 10.1128/JVI.01250-12. PubMed PMID: 22915798; PMCID: PMC3486308.
22. Fung T S, Liao Y, Liu D X. Regulation of Stress Responses and Translational Control by Coronavirus. Viruses. 2016; 8(7). Epub 2016 Jul. 8. doi: 10.3390/v8070184. PubMed PMID: 27384577; PMCID: PMC4974519.
23. Fung T S, Liu D X. The E R stress sensor IRE1 and MAP kinase ERK modulate autophagy induction in cells infected with coronavirus infectious bronchitis virus. Virology. 2019; 533:34-44. Epub 2019 May 15. doi: 10.1016/j.virol.2019.05.002. PubMed PMID: 31082732; PMCID: PMC7112053.
24. Yuan M, Wu N C, Zhu X, Lee C D, So R T Y, Lv H, Mok C K P, Wilson I A. A highly conserved cryptic epitope in the receptor-binding domains of SARS-CoV-2 and SARS-CoV. Science. 2020. Epub 2020 Apr. 5. doi: 10.1126/science.abb7269. PubMed PMID: 32245784.
25. Schoeman D, Fielding B C. Coronavirus envelope protein: current knowledge. Virol J. 2019; 16(1):69. Epub 2019 May 28. doi: 10.1186/s12985-019-1182-0. PubMed PMID: 31133031; PMCID: PMC6537279.
26. Wu Q, Zhang Y, Lu H, Wang J, He X, Liu Y, Ye C, Lin W, Hu J, Ji J, Xu J, Ye J, Hu Y, Chen W, Li S, Wang J, Wang J, Bi S, Yang H. The E protein is a multifunctional membrane protein of SARS-CoV. Genomics Proteomics Bioinformatics. 2003; 1(2):131-44. Epub 2005 Jan. 1. doi: 10.1016/s1672-0229(03)01017-9. PubMed PMID: 15626343; PMCID: PMC5172412.
27. Booth C M, Matukas L M, Tomlinson G A, Rachlis A R, Rose D B, Dwosh H A, Walmsley S L, Mazzulli T, Avendano M, Derkach P, Ephtimios I E, Kitai I, Mederski B D, Shadowitz S B, Gold W L, Hawryluck L A, Rea E, Chenkin J S, Cescon D W, Poutanen S M, Detsky A S. Clinical features and short-term outcomes of 144 patients with SARS in the greater Toronto area. JAMA. 2003; 289(21):2801-9. Epub 2003 May 8. doi: 10.1001/jama.289.21.JOC30885. PubMed PMID: 12734147.
28. Hanley B, Lucas S B, Youd E, Swift B, Osborn M. Autopsy in suspected COVID-19 cases. J Clin Pathol. 2020. Epub 2020 Mar. 22. doi: 10.1136/jclinpath-2020-206522. PubMed PMID: 32198191.
29. Xu Y H, Dong J H, An W M, Lv X Y, Yin X P, Zhang J Z, Dong L, Ma X, Zhang H J, Gao B L. Clinical and computed tomographic imaging features of novel coronavirus pneumonia caused by SARS-CoV-2. J Infect. 2020; 80(4):394-400. Epub 2020 Feb. 29. doi: 10.1016/j.jinf.2020.02.017. PubMed PMID: 32109443; PMCID: PMC7102535.
30. Moriyama M, Hugentobler W J, Iwasaki A. Seasonality of Respiratory Viral Infections. Annu Rev Virol. 2020. Epub 2020 Mar. 21. doi: 10.1146/annurev-virology-012420-022445. PubMed PMID: 32196426.
31. Pociask D A, Robinson K M, Chen K, McHugh K J, Clay M E, Huang G T, Benos P V, Janssen-Heininger Y M W, Kolls J K, Anathy V, Alcorn J F. Epigenetic and Transcriptomic Regulation of Lung Repair during Recovery from Influenza Infection. Am J Pathol. 2017; 187(4):851-63. Epub 2017 Feb. 15. doi: 10.1016/j.ajpath.2016.12.012. PubMed PMID: 28193481; PMCID: PMC5397680.
32. Hoffman S M, Chapman D G, Lahue K G, Cahoon J M, Rattu G K, Daphtary N, Aliyeva M, Fortner K A, Erzurum S C, Comhair S A, Woodruff P G, Bhakta N, Dixon A E, Irvin C G, Janssen-Heininger Y M, Poynter M E, Anathy V. Protein disulfide isomerase-endoplasmic reticulum resident protein 57 regulates allergen-induced airways inflammation, fibrosis, and hyperresponsiveness. J Allergy Clin Immunol. 2016; 137(3):822-32 e7. Epub 2015 Oct. 6. doi: 10.1016/j.jaci.2015.08.018. PubMed PMID: 26435004; PMCID: PMC4597791.
33. Chamberlain N, Anathy V. Pathological consequences of the unfolded protein response and downstream protein disulphide isomerases in pulmonary viral infection and disease. J Biochem. 2020; 167(2):173-84. Epub 2019 Dec. 4. doi: 10.1093/jb/mvz101. PubMed PMID: 31790139; PMCID: PMC6988748.
34. McCray P B, Jr., Pewe L, Wohlford-Lenane C, Hickey M, Manzel L, Shi L, Netland J, Jia H P, Halabi C, Sigmund C D, Meyerholz D K, Kirby P, Look D C, Perlman S. Lethal infection of K18-hACE2 mice infected with severe acute respiratory syndrome coronavirus. J Virol. 2007; 81(2):813-21. Epub 2006 Nov. 3. doi: 10.1128/JVI.02012-06. PubMed PMID: 17079315; PMCID: PMC1797474.
35. Yang X H, Deng W, Tong Z, Liu Y X, Zhang L F, Zhu H, Gao H, Huang L, Liu Y L, Ma C M, Xu Y F, Ding M X, Deng H K, Qin C. Mice transgenic for human angiotensin-converting enzyme 2 provide a model for SARS coronavirus infection. Comp Med. 2007; 57(5):450-9. Epub 2007 Nov. 3. PubMed PMID: 17974127.

Other Embodiments

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

The invention claimed is:

1. A method of treating a severe acute respiratory syndrome (SARS) virus infection, the method comprising administering to a subject in need thereof, a composition comprising a protein disulfide isomerase (PDI) inhibitor and a pharmaceutically acceptable excipient.

2. The method of claim 1, wherein the PDI inhibitor is a small molecule inhibitor, an anti-PDI antibody, or an inhibitory nucleic acid.

3. The method of claim 2, wherein the inhibitory nucleic acid is a small interfering RNA (siRNA).

4. The method of claim 1, wherein the PDI inhibitor is a protein disulfide isomerase A3 (PDIA3) inhibitor.

5. The method of claim 4, wherein the PDIA3 inhibitor is lead optimized compound 14 (LOC14).

6. The method of claim 4, wherein the PDIA3 inhibitor is selected from the group consisting of: PACMA31 and CCF642.

7. The method of claim 1, further comprising a second anti-viral component.

8. The method of claim 7, wherein the second anti-viral component is selected from the group consisting of: remdesivir, $\beta$-D-$N^4$-hydroxycytidine, convalescent plasma, Covid-19 monoclonal antibodies, and favipiravir.

9. The method of claim 1, wherein the SARS virus is a severe acute respiratory syndrome coronavirus 2 (SARS-CoV-2) virus.

10. The method of claim 4, wherein the PDIA3 inhibitor is a reversible inhibitor.

11. The method of claim 4, wherein the PDIA3 inhibitor is a selective PDIA3 inhibitor.

12. The method of claim 11, wherein the selective PDIA3 inhibitor binds with a higher affinity to PDIA3 than to PDIA1.

13. The method of claim 1, wherein the composition is administered to the subject orally, parenterally, by inhalation spray, topically, nasally, or via an implanted reservoir.

14. The method of claim 13, wherein the parenteral administration is selected from the group consisting of: subcutaneous, intracutaneous, intravenous, and intramuscular administration.

15. The method of claim 1, wherein the treating comprises reducing the subject's inflammatory response.

16. The method of claim 15, wherein levels of IL-6, TNF$\alpha$, IL-1$\beta$, and CCL2 in the subject are reduced relative to an untreated subject having a SARS virus infection.

17. The method of claim 1, wherein the treating comprises reducing acute lung injury (ALI), acute respiratory distress syndrome (ARDS), or ALI and ARDS.

18. The method of claim 1, the treating comprises reducing PDI bioactivity in the subject.

19. The method of claim 9, wherein the SARS-CoV-2 virus comprises a variant SARS-CoV-2 virus.

* * * * *